United States Patent [19]

Satoh et al.

[11] Patent Number: 5,053,490

[45] Date of Patent: Oct. 1, 1991

[54] USEFUL SUBSTANCE-ALBUMIN COMPLEX

[75] Inventors: Toshio Satoh; Hitoshi Matsumoto; Kakegawa Hisao, all of Tokushima, Japan

[73] Assignees: Nippon Hypox Laboratories Incorporated, Hachioji; Toshio Satoh, Tokushima, both of Japan

[21] Appl. No.: 323,150

[22] Filed: Mar. 13, 1989

Related U.S. Application Data

[63] Continuation of Ser. No. 945,571, Dec. 23, 1986, abandoned.

[30] Foreign Application Priority Data

Dec. 28, 1985 [JP] Japan .................................. 60-293451
Apr. 10, 1986 [JP] Japan .................................. 61-81118

[51] Int. Cl.$^5$ ............................................. A61K 37/02
[52] U.S. Cl. ...................................... 530/362; 514/21; 514/776

[58] Field of Search .................. 514/21, 776; 530/362

[56] References Cited

U.S. PATENT DOCUMENTS

| 2,194,188 | 3/1940 | Supplee | 530/365 X |
| 2,628,227 | 2/1953 | Ames | 530/367 X |
| 2,789,080 | 4/1957 | Christensen | 424/101 X |
| 4,067,963 | 1/1978 | Ishii | 530/362 X |
| 4,195,126 | 3/1980 | Hall | 435/11 |

Primary Examiner—Howard E. Schain
Assistant Examiner—Choon P. Koh
Attorney, Agent, or Firm—Venable, Baetjer, Howard & Civiletti

[57] ABSTRACT

A powdery complex is obtained by combining a useful substance such as vitamin E and liquid fatty oil with albumin. This powdery complex has excellent storage stability and can keep the useful substance contained therein stably for a long time.

6 Claims, No Drawings

USEFUL SUBSTANCE-ALBUMIN COMPLEX

This application is a continuation of application Ser. No. 06/945,571, filed on Dec. 23, 1986, now abandoned.

BACKGROUND OF THE INVENTION

1. Field of the Invention

This invention relates to a useful substance-albumin complex.

2. Description of Prior Art

The useful substance used for forming a complex with albumin in this invention is selected from substances such as vitamin E and liquid fatty oils, so, first of all, the problems of the prior art have been recognized in processing these useful substances for use as or in pharmaceutical preparations or foods are reviewed severally for each type of substance.

Vitamin E

Vitamin E is popularly used as a therapeutic or prophylatic agent for habitual abortion, peripheral vascular trouble and heart diseases. However, vitamin E per se is a light-yellow viscous oily substance and very susceptible to oxidation, so that great difficulties were involved in processing of this substance for use as or in pharmaceutical preparations or foods. Various methods have been proposed for powdering or improvement of storage stability of vitamin E. For instance, Japanese Patent Publication No. 38348/70 discloses a method for obtaining a fat-soluble vitamin powder by mixing a reducing sugar and an amino acid in an emulsion containing a fat-soluble vitamin and thereafter heat-drying the mixture to produce a reaction product of said sugar and amino acid. Also, Japanese Patent Publication No. 21403/79 reports a method for obtaining a powdery vitamin E preparation by mixing lactobacillus-treated soybean milk with vitamin E and drying the mixture. For these preparations, however, because of their hygroscopicity, it was necessary to add dextrin or starch as a moisture absorption preventive agent in the course of manufacturing process or to add a desiccant during storage.

Thus, the realization of vitamin E preparations having excellent storage stability has been desired.

Fatty oils

Fatty oils are a substance which the organisms store as a nutrient source for their life and which is also contained in all sorts of plant seeds and animal bodies. Therefore, there exist a great variety of fatty oils, and their properties and use are different from one another.

Fatty oils can be classified into vegetable oils and animal oils according to the difference of base material, and they contain various types of fatty acids. Most of the animals need poly-unsaturated fatty acids for maintaining the normal structure and function. Further, since they cannot make in vivo the poly-unsaturated fatty acids from saturated fatty acids or mono-unsaturated fatty acids, it is necessary for them to take in such unsaturated substance from external sources. Fish oils such as lamprey oil, sardine oil and herring oil contain vitamins and various kinds of fatty acids and are popularly used as nutritious food. Eicosapentaenoic acid (EPA) and docosahexaenoic acid (DHA) are used for the prevention and treatment of myocardial infarction and thrombotic trouble. It is also known that these acids have a serum cholesterol reducing action, and their pharmaceutical preparations are commercially available as soft capsules.

It was further found recently that the saturated fatty acids having 13-15 and 21 carbon atoms, oleic acid, linolic acid and linolenic acid have an anti-cancer activity. Since these fatty acids however are unstable against oxidation, their processing for use as pharmaceutical preparations or foods was difficult. Therefore, various methods have been tried for preparing them into soft capsules or using them in the form of a suspension.

Concerning use as a suspension, there is known, for instance, a fat infusion comprising a fatty acid or an ester thereof suspended in a vegetable oil, an emulsifier and water (see Japanese Patent Kokai (Laid-Open) No. 237017/85).

Such suspension, however, especially those containing a large amount of water, had the problems on transport and storage.

On the other hand, soft capsules had the problem that, after taken, they would cause belching and an unpleasant smell would remain in the mouth, because the encapsulated fatty oil is usually insoluble in water and contains a fatty acid with a high degree of unsaturation and such fatty acid would be oxidized and decomposed by oxygen in the air to produce a malodorous substance.

Manufacture of a powdery preparation from a liquid fatty oil by supporting such oil on a carrier may have been tried in the past, but there is yet available no powdery preparation of liquid fatty oil with excellent storage stability.

The object of this invention, therefore, is to provide a novel preparation which can be preserved in a stable form without causing any change in quality of useful substance contained therein such as vitamin E and liquid fatty oil.

Other object of the invention will become apparent from the following description.

SUMMARY OF THE INVENTION

As a result of extensive studies for attaining said object of the invention, the present inventors have now found that a complex obtained by combining albumin with useful substance such as vitamin E and liquid fatty oil is insoluble in water, non-hygroscopic and also excellent in storage stability.

Thus, the present invention provides a powdery complex of useful substance with albumin, the typical examples of said useful substance are vitamin E and liquid fatty oils. Oily dye may be used as the substance.

In the prior art concerning pharmaceutical use of albumin, Japanese Patent Kokai (Laid-Open) No. 216126/83 discloses use of human serum albumin as a solubilizing agent for water-insoluble or sparingly water-soluble pharmaceuticals. The disclosed technique of this patent, however, consists in making use of the pharmaceutical solubilizing action of human serum albumin and is quite alien to the technical concept of the present invention which consists in preparing a water-insoluble complex by reacting useful substance with albumin. Also, this prior patent discloses nothing about vitamin E and liquid fatty oils.

The present invention will be described more particularly below.

The useful substance to be combined with albumin to form a complex in this invention includes substances which are useful for animals especially human beings, such as vitamin E, liquid fatty oils and oily dyes.

As vitamin E, naturally existing α-, β-, γ- and δ-tocopherol may be mentioned as typical examples. Optical isomers of d-, l- and dl-compounds of said tocopherols are also usable. It is further possible to use synthetic vitamin E esters such as acetic ester and nicotinic ester.

As the liquid fatty oil, there can be used any type of fats, fatty acids and animal or vegetable oils containing them provided that they are liquid at normal temperature or can be rendered into a liquid state by heating or dissolving them in a solvent. The fatty acids usable in this invention include saturated and unsaturated fatty acids. As examples of saturated fatty acids, there can be cited the fatty acids having 2 to 26 carbon atoms, among which palmitic acid, stearic acid, lauric acid and myristic acid are especially preferred. Examples of unsaturated fatty acids are the fatty acids having 10 to 22 carbon atoms, among which palmitoleic acid, oleic acid, linolic acid, linolenic acied, eicosapentaenoic acid, docosahexaenoic acid and arachidonic acid are advantageous. The animal oils usable in this invention include sardine oil, herring oil, cod oil, shark oil, cuttlefish oil, whale oil, dolphin oil, crucian oil, carp oil, eel oil, lamprey oil, krill oil, chrysalis oil and beef foot oil. The vegetable oils include sesame oil, olive oil, rape oil, soybean oil, cottonseed oil, rice oil, corn oil, evening primrose oil, safflower oil and castor oil.

- As the oily dye, there can be used any oily dye for foods, cosmetics, etc.

As the albumin to be combined with said substance for forming a complex in this invention, there can be used, for instance, egg albumin, serum albumin, plakalbumin, α-lactalbumin, leucosin, phaselin and levumelin. Use of human derived albumin is especially preferred where the complex of this invention is applied to the type of medicines in which antigenecity is a matter of concern.

The complex of this invention can be easily produced by first dissolving albumin in an aqueous solution and then adding said useful substance in the solution to let the two materials contact each other.

In the preparation of said complex, the concentration of the albumin in the aqueous solution is not critical, but preferably it is at least 1% (W/V), more preferably 5 to 25% (W/V). The ratio of albumin to useful substance is also not critical but can be varied over a wide range provided that their reaction can form a precipitate, but usually it is preferred to use albumin in a ratio of 100 parts to 5-200 parts of useful substance.

As for the aqueous solution in which albumin is dissolved, it is possible to use any proper type of aqueous soution which is capable of dissolving albumin without causing any denaturation thereof, but water is the most preferred. A part of water may be substituted with a water-soluble solvent such as ethanol, propylene glycol, glycerin and the like.

The reaction temperature and reaction time are not critical but can be changed according to the type of albumin and useful substance used, but generally it is advantageous to carry out their reaction under stirring at a temperature which can keep the useful substance in a liquid state and will not cause any thermal denaturation of albumin, preferably at room temperature for about 1 to 30 hours.

Both useful substance and albumin are reacted approximately 100% regardless of their added amount ratio, and the reaction forms a precipitate having the useful substance combined in a ratio of 5-250% to albumin according to the their added amount ratio.

The thus obtained precipitate is then freed of solvent by suitable means such as air drying, drying in vacuo, drum drying, spray drying, etc., to obtain the objective powdery useful substance-albumin complex.

The complex of this invention obtained in the manner described above is non-hygroscopic, insoluble in water and also stable lastingly in spite of the fact that it is made of natural products. Therefore, this complex is easy to work into various forms of preparation. For instance, it can be worked itno tablets or sheet-like preparations with additives generally used for pharmaceutical preparations, such as excipien, binder, disintegrator, lubricant, etc. Also, said complex can be mixed uniformly with other powders and thus can be applied to use for foods, cosmetics, pharmaceuticals, livestock feed, etc.

The present invention will be further described below by showing examples thereof, which examples are however merely intended to be illustrative and not limitiv  the scope of the invention.

EXAMPLE 1 (VITAMIN E-ALBUMIN COMPLEX)

Five grams of egg albumin was dissolved in 100 ml of water, and the resulting solution was added with 1 g of dl-α-tocopherol and stirred at room temperature for 24 hours. Then the solution was dried by using a spray dryer to obtain 4.3 g of a white powdery dl-α-tocopherol-egg albumin complex [tocopherol to albumin bonding ratio (measured by the vitamin E determination method described below)=1:5].

The obtained powdery vitamin E-albumin complex was put into the brown bottles and kept in the sealed bottles at room temperature for the periods of one month, 6 months, 12 months and 18 months, and the percentage of the amount of vitamin E which remained after said periods of storage was measured according to the vitamin E determination method shown below. Non-treated dl-α-tocopherol was used as control.

Vitamin E determination method

Since the vitamin E and albumin bonding force in the vitamin E-albumin complex of this invention is very strong, it is impossible to perfectly extract vitamin E by the ordinarily used chloroform-methanol extraction method. Therefore, the vitamin E to albumin bonding ratio in the complex and the percentage of the remaining amount of vitamin E were measured by the following method.

two - ten grams of vitamin E-albumin complex was precisely weighed and put into a 200 ml eggplant type flask. Then 10-50 ml of water was added thereto, followed by the addition of bioplase in an amount equivalent to 1% of the weight of the vitamin E-albumin complex, and the mixture was stirred at 40° C. for 1-2 hours. Then vitamin E was extracted by adding 30-100 ml of chloroform-methanol (2:1) solution, and the chloroform-methanol layer was washed with water and dried over magnesium sulfate. Then the solvent was distilled off under reduced pressure in a nitrogen gas atmosphere. The residue was dissolved in methanol to obtain accurately 50 ml of the nethanolic solution, which was then subjected to quantitative determination by liquid chromatography (column: Zorbax ODS (registered trade name), 4.6 mm in inner diameter and 250 mm in length; moving bed: methanol/water (95/5); room temp., moving bed speed =1.0 ml/min; detector: UV 254 nm).

The results are shown in Table 1.

TABLE 1

| Period of storage (months) | Vitamin E-egg albumin complex (%) | dl-α-tocopherol (control) (%) |
| --- | --- | --- |
| 1 | 100 | 98 |
| 6 | 98 | 95 |
| 12 | 96 | 88 |
| 18 | 91 | 83 |

As seen from Table 1, the vitamin E-albumin complex of this invention is small in reduction with time of the remaining amount of vitamin E in the complex, indicating very excellent keeping quality (long-lasting stability) of the complex.

EXAMPLE 2 (VITAMIN E-ALBUMIN COMPLEX)

Five grams of egg albumin was dissolved in 100 ml of water, and this solution was added with 10 g of dl-α-tocopherol and stirred at room temperature for 24 hours. The resulting reaction solution was added with 100 ml of ethanol and dried in vacuo to obtain 3.5 g of a white powdery dl-α-tocopherol-egg albumin complex (tocopherol to albumin bonding ratio=1:0.5).

The obtained vitamin E-albumin complex showed as excellent lasting stability as the complex of Example 1.

EXAMPLE 3 (FATTY OIL-ALBUMIN COMPLEX)

Ten grams of egg albumin was dissolved in 100 ml of water, and this solution was added with 5 g of lamprey oil and stirred at room temperature for 24 hours. The resulting reaction solution was added with 100 ml of ethanol and dried in vacuo to obtain 14.9 g of a light-brown powdery lamprey oil-egg albumin complex (lamprey oil to albumin bonding ratio=0.5:1).

EXAMPLE 4 (FATTY OIL-ALBUMIN COMPLEX)

Five grams of egg albumin was dissolved in 100 ml of water, and this solution was added with 1 g of γ-linolenic acid and stirred at room temperature for 24 hours. The reulsting solution was dried by using a spray dryer to obtain 4.3 g of a white powdery γ-linolenic acid-egg albumin complex (γ-linolenic acid to albumin bonding ratio=1:5).

EXAMPLE 5 (FATTY OIL-ALBUMIN COMPLEX)

Five grams of egg albumin was dissolved in 100 ml of water, and this solution was added with 2.5 g of olive oil and stirred at high speed at room temperature for 15 minutes. The resulting reaction solution was added with 50 ml of ethanol and, after distilling off the solvent, the solution was dried in vacuo to obtain 7.4 g of a slightly yellowish white powdery olive oil-egg albumin complex (olive oil to albumin bonding ratio=1:2).

EXAMPLE 6 (FATTY OIL-ALBUMIN COMPLEX)

Five grams of egg albumin was dissolved in 100 ml of water, and this solution was added with 3.0 g of evening primrose oil and stirred at high speed at room temperature for 15 minutes. The resulting reaction solution was added with 50 ml of ethanol and dried in vacuo to obtain 7.9 g of a slightly yellowish white powdery evening primrose-egg albumin complex (evening primrose oil to albumin bonding ratio=0.6:1).

The fatty oil-albumin complexes produced in Examples 3-6 were put into the respective aerated bottles and stored at 40° C. and 75% RH for the periods of 30 days, 60 days and 90 days, and the content of fatty oil in the complex was measured as an index of weight change after said periods of storage.

Method of fatty oil extraction and determination

One to three gram(s) of fatty oil-albumin complex was precisely weighed and put into a 200 ml eggplant type flask. Then 2-6 ml of water was added thereto, followed by further addition of 50-150 ml of a chloroform-methanol (2:1) solution, and the mixture was heated under stirring over a water bath (60°-65° C.) in a nitrogen gas atmosphere for 1-2 hours, with a Dimroth condenser attached to the flask. After cooling, the thus treated mixed solution was filtered and the residue was washed 2 to 3 times with 25 ml of said chloroform-methanol solution. The washings and the filtrate were combined, and the combined solution was concentrated under reduced pressure in a nitrogen gas atmosphere until a viscous liquid was formed. The residue was added with 50 ml of petroleum ether or ether and filtered by using Watman IPS Filter Paper (registered trade name). Then the solvent was distilled off from the filtrate under a nitrogen gas atmosphere and its weight (g) was measured.

The result are shown in Table 2. The figures in the table show the content of fatty oil in the complexes obtained by the methods of Examples 3-6.

TABLE 2

| | (unit: %) | | | |
| --- | --- | --- | --- | --- |
| Sample | At the time of preparation | 30 days | 60 days | 90 days |
| Example 3 Lamprey oil-albumin (0.5:1) | 33.5 | 33.6 | 34.0 | 34.4 |
| Example 4 γ-linolenic acid-albumin (1:5) | 16.7 | 16.6 | 16.4 | 16.1 |
| Example 5 Olive oil-albumin (1:2) | 33.3 | 33.3 | 33.1 | 32.9 |
| Example 6 Evening primrose oil-albumin (0.6:1) | 37.5 | 37.6 | 37.7 | 38.9 |

As seen from Table 2, the fatty oil-albumin complexes of this invention are almost unchanged in fatty oil content even after the lapse of 90 days (from the date of preparation) and thus have excellent long-time stability.

The lamprey oil-albumin (0.5:1) complex, which is most susceptible to rancidity among the fatty oil-albumin complexes obtained according to this invention, was put into an aerated bottled and kept at 40° C. and 75% RH for 30 days, then the fatty acid was extracted in the same way as described above and its peroxide value, acid value and iodine value were determined by the methods shown below. Used as control was the non-treated lamprey oil which was kept under the same conditions for 30 days.

Determination of peroxide value (POV)

One gram of fatty oil obtained by said fatty oil extraction method (this fatty oil being hereinafter referred to as sample oil) was precisely weighed and put into a 200 ml ground stopper flask. Then 25 ml of an acetic acid-carbon tetrachloride (3:2) solution was added thereto, followed by further addition of 0.5 ml of a saturated potassium iodide solution, and the flask was shaken gently for 2 minutes. Thereafter, 50 ml of water was added and the mixed solution was titrated with a 0.01N sodium thiosulfate reagent.

$$POV = \frac{A \times F}{T} \times 10$$

A: 0.01N sodium thiosulfate reagent (ml),
F: factor,
T: sample oil (g).

Determination of acid value (AV)

One gram of sample oil was precisely weighed and put into a 250 ml ground stopper flask, and after adding thereto 100 ml of a benzene-ethanol (1:1) solution and 1 to 2 drops of phenolphthalein reagent, the mixed solution was titrated with a 0.1N sodium hydroxide-ethanol solution.

$$AV = \frac{B \times 5.611 \times F}{T}$$

B: 0.1N sodium hydroxide-ethanol (ml),
F: factor,
T: sample oil (g).

Determination of iodine value (IV)

Sample oil (0.1–0.15 g) was precisely weighed and put into a 500 ml ground stopper flask, and after adding thereto 10 ml of carbon tetrachloride, the flask was shaken. Then precisely 25 ml of an iodine trichloride reagent was added thereto, and after stoppered, the flask was left in a dark place for one hour, said flask being shaken from time to time. Then 20 ml of a potassium iodide solution was added, followed by further addition of 100 ml of water, and after sufficient shaking, the mixed solution was titrated with a 0.1N sodium thiosulfate solution. 1 ml of a starch reagent was used as indicator. A blank test was conducted under the same conditions.

$$IV = \frac{(A - B) \times 1.269}{T}$$

A: amount of 0.1N sodium thiosulfate reagent in the blank test (ml),
B: amount of 0.1N sodium thiosulfate reagent in the sample oil (ml),
T: sample oil (g).

The results of determination of peroxide value (POV), acid value (AV) and iodine value (IV) are shown in Table 3.

TABLE 3

|  | At the time of preparation | After lapse of 30 days | |
|---|---|---|---|
|  |  | Complex of this invention | Control |
| Peroxide value (POV) | 0.5 | 40.4 | 354 |
| Acid value (AV) | 0.14 | 2.02 | 12.03 |
| Iodine value (IV) | 178 | 168 | 167 |

As seen from Table 3, the fatty oil-albumin complex of this invention, unlike the control, is not sharply increased in peroxide value and acid value with the lapse of time and has excellent long-time stability.

The long-time stability of the lamprey oil-albumin (0.5:1) complex was confirmed not only by the determination of POV, Av and IV but also by gas chromatographic analysis conducted as mentioned below.

The lamprey oil-albumin complex after stored for 2 months was subjected to chloroform-methanol extraction in the same way as described above, and the extract obtained was analysed with a gas chromatograph Shimadzu GC-9A to determine the fatty acid composition thereof.

| Gas Chromatograph Conditions | |
|---|---|
| Gas chromatograph | Shimadzu GC-9A |
| Integrator | Shimadzu C-R1B |
| Detector | FID |
| Column | 5% Advance - DS on Chromosorb W (AW-DMCS) 00–100 mesh, Glass 3 mm × 3 m |
| Temperature | Inlet port 260° C. Column 180 - 225° C. (3° C./min) Detector 260° C. |
| Gas Flow Rate | $N_2$ - 50 ml/min, $H_2$ - 0.6 kg/cm$^2$, Air - 0.5 kg/cm$^2$ |

Used as control was lamprey oil per se which was employed as a starting material in the preparation of the lamprey oil-albumin complex.

The results of the gas chromatographic analysis are shown in Table 4.

TABLE 4

| Fatty acid component | lamprey oil per se (control) | lamprey oil-albumin complex after 2 months storage |
|---|---|---|
|  | % | % |
| $C_{14}$ | 6.1 | 6.3 |
| $C_{15}$ | 0.5 | 0.5 |
| $C_{16}$ | 13.1 | 12.2 |
| $C_{16:1}$ | 10.2 | 9.8 |
| $C_{17:1}$ | 1.2 | 1.0 |
| $C_{18}$ | 1.4 | 1.1 |
| $C_{18:1}$ | 20.9 | 17.8 |
| $C_{18:2}$ | 2.9 | 3.1 |
| $C_{20}$ | 0.5 | 0.7 |
| $C_{18:3} + C_{20:1}$ | 5.8 | 4.9 |
| $C_{18:4}$ | 2.9 | 2.9 |
| $C_{20:4\omega6} + C_{22:1}$ | 2.3 | 3.2 |
| $C_{20:4\omega3}$ | 1.7 | 2.3 |
| EPA ($C_{20:5}$) | 11.1 | 11.9 |
| $C_{24:1}$ | 1.7 | 2.7 |
| $C_{22:5}$ | 2.9 | 3.6 |
| DHA ($C_{22:6}$) | 11.0 | 10.1 |

As seen from Table 3, the fatty acid composition in the lamprey oil-albumin complex was retained without causing significant change even after stored for 2 months, which means that the fatty oil-albumin complex of the present invention has long-time stability.

What is claimed is:

1. A composition which comprises a water-insoluble powdery complex of albumin and a useful substance selected from the group consisting of vitamin E, and liquid fatty oil in a ratio of 5-200 parts of the useful substance of 100 parts of the albumin.

2. A composition according to claim 1, wherein vitamin E is dl-α-tocopherol.

3. A composition according to claim 1, wherein the liquid fatty oil is a saturated fatty acid having 6-24 carbon atoms.

4. A composition according to claim 1, wherein the liquid fatty oil is selected from the group consisting of palmitoleic acid, oleic acid, linolic acid, linolenic acid, eicosapentaenoic acid and docosanhexaenoic acid.

5. A composition according to claim 1, wherein the liquid fatty oil is lamprey oil.

6. A composition according to claim 1, wherein the albumin is egg albumin.

* * * * *